(12) United States Patent
Vaidyanathan

(10) Patent No.: US 9,327,057 B1
(45) Date of Patent: May 3, 2016

(54) MEDICAL DEVICES HAVING MRI COMPATIBLE METAL ALLOYS

(71) Applicant: University of Central Florida Research Foundation, Inc., Orlando, FL (US)

(72) Inventor: Rajan Vaidyanathan, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 16 days.

(21) Appl. No.: 14/158,444

(22) Filed: Jan. 17, 2014

Related U.S. Application Data

(62) Division of application No. 12/629,723, filed on Dec. 2, 2009, now Pat. No. 8,644,951.

(60) Provisional application No. 61/119,091, filed on Dec. 2, 2008.

(51) Int. Cl.

| A61L 31/18 | (2006.01) |
|---|---|
| A61F 2/06 | (2013.01) |
| A61L 31/14 | (2006.01) |
| A61L 31/02 | (2006.01) |
| A61N 1/08 | (2006.01) |

(52) U.S. Cl.
CPC ............... *A61L 31/022* (2013.01); *A61N 1/08* (2013.01)

(58) Field of Classification Search
CPC ..... A61L 31/18; A61L 2400/12; A61L 27/50; A61L 27/06; A61L 31/022; A61N 2001/086; A61B 10/0283
USPC ......................................... 607/116; 623/1.15
See application file for complete search history.

(56) References Cited

U.S. PATENT DOCUMENTS

| 6,506,972 | B1 | 1/2003 | Wang |
| 6,673,999 | B1 | 1/2004 | Wang et al. |
| 6,713,671 | B1 | 3/2004 | Wang et al. |
| 6,718,207 | B2 | 4/2004 | Connelly |
| 6,765,144 | B1 | 7/2004 | Wang et al. |
| 6,795,736 | B2 | 9/2004 | Connelly et al. |
| 6,844,492 | B1 | 1/2005 | Wang et al. |
| 6,846,985 | B2 | 1/2005 | Wang et al. |
| 6,847,837 | B1 | 1/2005 | Melzer et al. |

(Continued)

OTHER PUBLICATIONS

Heimann, R. B. "Thermal spraying of biomaterials." Surface and Costings Technology 201.5 (2006): 2012-2019.

(Continued)

*Primary Examiner* — Carl H Layno
*Assistant Examiner* — Erin M Piateski
(74) *Attorney, Agent, or Firm* — Jetter & Associates, P.A.

(57) ABSTRACT

An MRI compatible medical device includes a non-magnetic metal alloy portion having a bulk portion including a first and a second metal. A surface of the metal alloy portion includes an integral MRI heating resistant surface structure having a thickness ≥3 nanometers. The non-magnetic metal alloy portion is structurally different from the bulk portion and includes a lamellar nanostructure or microstructure. The MRI heating resistant surface structure can include (i) a matrix phase including the first and second metal having nanometer or micron scale particles, precipitates and/or inclusions that differ in chemical composition and physical characteristics of the matrix phase and are discontinuously distributed therein; (ii) a level of crystallinity at least 5% less than the bulk portion; and/or (iii) metal atoms different from the first and second metal having a concentration profile evidencing diffusion into the metal alloy portion.

13 Claims, 4 Drawing Sheets

(56) References Cited

U.S. PATENT DOCUMENTS

| | | |
|---|---|---|
| 6,876,886 B1 | 4/2005 | Wang |
| 6,906,256 B1 | 6/2005 | Wang |
| 6,930,242 B1 | 8/2005 | Helfer et al. |
| 6,980,865 B1 | 12/2005 | Wang et al. |
| 7,010,357 B2 | 3/2006 | Helfer et al. |
| 7,091,412 B2 | 8/2006 | Wang et al. |
| 7,127,294 B1 | 10/2006 | Wang et al. |
| 7,162,302 B2 | 1/2007 | Wang et al. |
| 2004/0116800 A1 | 6/2004 | Helfer et al. |
| 2004/0249428 A1* | 12/2004 | Wang ................ A61F 2/90 607/116 |
| 2007/0032862 A1 | 2/2007 | Weber et al. |
| 2007/0044871 A1 | 3/2007 | Stinson |
| 2008/0071347 A1* | 3/2008 | Cambronne ............. 623/1.15 |
| 2008/0195194 A1* | 8/2008 | Pacetti et al. ............. 623/1.16 |
| 2009/0198314 A1* | 8/2009 | Foster .............. A61N 1/056 607/127 |

OTHER PUBLICATIONS

Kim et al. "Observation of the failure mechanism for diamond-like carbon film on stainless steel under tensile loading." Scripta Materialia 57.11 (2007): 1016-1019.

\* cited by examiner

MEDICAL DEVICES HAVING MRI COMPATIBLE METAL ALLOYS

CROSS REFERENCE TO RELATED APPLICATIONS

This application is a divisional application of U.S. nonprovisional patent application Ser. No. 12/629,723 entitled "MEDICAL DEVICES HAVING MRI COMPATIBLE METAL ALLOYS" filed Dec. 2, 2009, now U.S. Pat. No. 8,644,951, which claims the benefit of Provisional Application Ser. No. 61/119,091 entitled "METALLIC ALLOYS AND DEVICES WITH IMPROVED MRI COMPATIBILITY AND METHODS FOR FABRICATING THE SAME", filed Dec. 2, 2008, which is herein incorporated by reference in its entirety.

FIELD

Disclosed embodiments relate to medical devices including non-magnetic metal alloys, including methods for fabricating such alloys, wherein the alloys provide enhanced MRI compatibility.

BACKGROUND

Magnetic Resonance Imaging (MRI) is a commonly used diagnostic tool to image soft tissues in the human body. MRI systems use strong magnetic fields. The strong magnetic fields can attract ferromagnetic objects with significant force and torque while the pulsed gradient and radio frequency (RF) fields may induce currents that can produce significant heating in metallic objects. For example, Sommer et al. (Sommer T, Vahlhaus C, Lauck G, von Smekal A, Reinke M, Hofer U, Block W, Traber F, Schneider C, Gieseke J, Jung W, Schild H: MR imaging and cardiac pacemakers: in-vitro evaluation and in-vivo studies in 51 patients at 0.5 T Radiology 2000, 215(3):869-79.4) demonstrated the potential for induced heating as much as 23.5° C. at specific absorption rate (SAR) levels of only 1.3 W/kg in a 0.5 Tesla MRI unit.

A desirable patient for an MRI procedure (e.g. MRI scan) is one who does not have any metallic medical devices implanted in his or her body that would thus avoid interaction with the magnetic and RF fields associated with the MRI scan. However, a significant percentage of potential patients for MRI have implanted medical devices such as pacemaker leads, stents, clips, plates, and joint prostheses. Even if the metal in the implanted device is non-ferromagnetic, the RF field associated with the MRI procedure can lead to harmful heating effects as a result of the RF induced currents in the metal. Hence there is a need for metal alloys for medical devices that are less susceptible to such harmful heating effects. Conventional solutions to the MRI interaction problem have generally relied on coatings or resonator technologies external to the implanted device, such as copper windings.

MRI can also be used for imaging of implanted medical devices during a medical procedure. Medical devices are generally defined as products used for medical purposes in patients, in diagnosis, therapy or surgery. If applied to the body, the effect of the medical device is primarily physical, in contrast to pharmaceutical drugs, which exert a biochemical effect.

Examples of imaging of implanted medical devices during a medical procedure include real-time imaging while placing a stent, using a catheter or other medical device in the human body. It may also include post-implant imaging of the implanted stent or other medical device during the life of the patient. In such cases the medical implant may not be visible clearly in MRI resulting in imaging artifacts such as areas of poor or no contrast, or in some cases even not providing visibility through the device. An example is struts of a stent which do not allow for any image of the tissue or blood vessel between the struts, but the entire stent images without any difference between the strutted and the non-strutted region. Hence there is also a need for metal alloys for medical devices that are less susceptible to such imaging artifacts and poor visibility.

The availability of medical devices having enhanced MRI compatibility devices could enable their extension and incorporation into a suite of medical instruments (e.g., guide wires, catheters, needles, etc.) that would facilitate MRI interventional procedures without the need to examine the patient for possible different types of contraindications that would prevent a person from being examined with an MRI scanner. Such procedures could also replace more traditional fluoroscopic procedures, thereby minimizing the patient's and the physician's exposure to harmful radiation.

SUMMARY

This Summary is intended to only present a summary of this disclosure to briefly indicate the nature and substance of the subject matter disclosed herein. It is submitted with the understanding that it will not be used to interpret or limit the scope or meaning of the claims.

Embodiments of the invention describe MRI compatible medical devices that have an MRI compatible medical device which includes a non-magnetic metal alloy portion having a bulk portion including a first and at least a second metal different from the first metal. A surface of the metal alloy portion includes an integral MRI heating resistant surface structure having a thickness ≥3 nanometers. The non-magnetic metal alloy portion is structurally different from the bulk portion and includes a lamellar nanostructure or microstructure.

The MRI heating resistant surface structure can be compositionally different from the bulk portion and include one or more of (i) a matrix phase including the first and second metal having nanometer or micron scale particles, precipitates and/or inclusions constituting a volume fraction ≥3%, wherein the particles, precipitates or inclusions differ in chemical composition and physical characteristics of the matrix phase and are discontinuously distributed therein; (ii) a level of crystallinity at least 5% less as compared to a level of crystallinity in the bulk of the metal alloy portion; (iii) metal atoms different from the first and second metal having a concentration profile evidencing diffusion into the metal alloy portion, such as by adding suitable additional metals, such as Au, Pt, Pd or Ag.

Significantly, the skin depth of the interaction between the RF wave during MRI has been found by the Inventors to be altered by the MRI heating resistant surface structure of the metallic alloy or device so as to reduce the energy absorbed during MRI that is available to induce a current, thus reducing heating. Moreover, it has also been found by the Inventors that the MRI heating resistant surface structure of the metallic alloy or device has an altered impedance that results in reduced heating from the current induced by the RF field.

BRIEF DESCRIPTION OF THE DRAWINGS

FIG. 1A is a depiction of an exemplary partially cut open medical device that includes a battery, wherein a metal alloy portion includes an MRI heating resistant surface structure that provides leads that are coupled to the battery for carrying current from the battery, while

FIG. 2A is a depiction of an exemplary non-current carrying medical device, wherein a metal alloy portion includes an MRI heating resistant surface structure, while

DETAILED DESCRIPTION

Figure 1A:
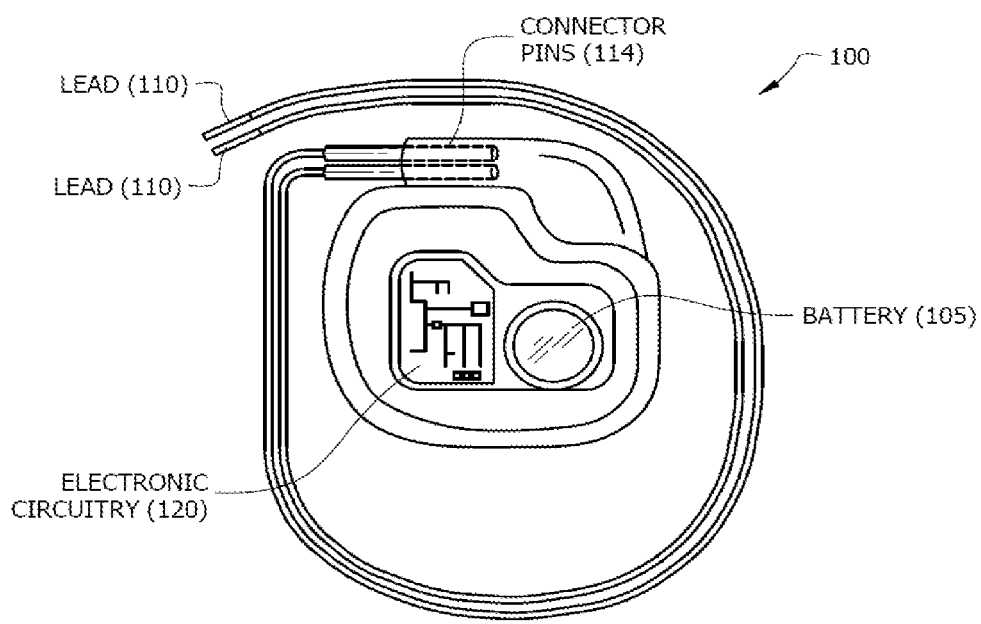

Disclosed embodiments are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments. One having ordinary skill in the relevant art, however, will readily recognize that the disclosed embodiments can be practiced without one or more of the specific details or with other methods. In other instances, well-known structures or operations are not shown in detail to avoid obscuring certain details. The disclosed embodiments are not limited by the illustrated ordering of acts or events, as some acts may occur in different orders and/or concurrently with other acts or events. Furthermore, not all illustrated acts or events are required to implement a methodology in accordance with the disclosed embodiments.

Disclosed embodiments comprise medical devices having at least one non-magnetic metal alloy portion, wherein the metal alloy portion comprises a first and at least a second metal different from the first metal. A surface of the metal alloy portion includes an integral MRI heating resistant surface structure that has thickness ≥3 nanometers to provide improved MRI compatibility for the medical device. The heat generating reducing layer is an integral layer that is integral with the metal alloy or device since it is provided by processing performed to the metal alloy or device described below, as opposed to non-integral layer(s) that are deposited onto the metal alloy or device in the form of a coating, or are adhesively joined or fastened, or wound around.

Exemplary medical devices or portions thereof that can benefit from disclosed embodiments include, but are not limited to, those which are coupled to a power supply such as a battery and are current carrying such as cardiac leads (e.g., for pacemaker devices), neuro-stimulator leads (for neuro-stimulator devices), and non-current carrying such as clips, staples, markers, stents, catheters, guide wires, screws, bolts, orthopedic implants, cochlear implants, and valves.

For purposes of describing disclosed embodiments, "improved MRI compatibility" is defined as follows:
1. Reduced heating due to the gradient and RF fields associated with an MRI environment (when compared to alloys or devices known in the art and permissible under existing government, e.g. the U.S. FDA guidelines), as measured by ASTM F2182-02a for Measurement of Measurement of Radio Frequency Induced Heating Near Passive Implants During MRI, 2006); and
2. Reduced imaging artifacts (when compared to alloys or devices known in the art and permissible under existing government, e.g. the U.S. FDA guidelines), as measured by ASTM F2119-01 for Evaluation of MR Image Artifacts from Passive Implants, 2006).

Improved MRI compatibility also generally includes:
3. Reduced displacement due to a magnetic field associated with an MRI environment when compared to alloys or devices known in the art and permissible under existing government, e.g. the U.S. FDA guidelines), as measured by ASTM F2052-06 for Measurement of Magnetically Induced Displacement Force on Medical Devices in the MR Environment and ASTM F2213-06 for Measurement of Magnetically Induced Torque on Medical Devices in the MR Environment, 2006.

Methods are disclosed herein for fabricating non-magnetic metallic alloys with improved MR compatibility that can be used for medical implants and devices, or to improve the MR compatibility of metallic alloys that have already been formed into medical implants and devices. As used herein "non-magnetic" refers to acceptable behavior in a magnetic field following ASTM standard documents F2052-06 for Measurement of Magnetically Induced Displacement Force on Medical Devices in the MR Environment (2006), and F2213-06 for Measurement of Magnetically Induced Torque on Medical Devices in the MR Environment (2006). If the magnetically induced deflection force is less than the force on the device or metal alloy due to gravity (its weight), it is considered acceptable behavior or "non-magnetic" herein since the risk imposed by the application of the magnetically induced force is no greater than the risk imposed by normal daily activity in the Earth's gravitational field.

The MRI heating resistant surface structure is provided at the surface of the metal alloy or device, and is optionally in its bulk as well. The MRI heating resistant surface structure comprises at least one of:

(i) a matrix phase comprising said first and said second metal having a plurality of nanometer scale to micron scale particles, precipitates and/or inclusions therein constituting a volume fraction ≥3%, wherein said particles, precipitates or inclusions differ in chemical composition and physical characteristics from said matrix phase and are discontinuously distributed therein;

(ii) a level of crystallinity that is at least 5% less as compared to a level of crystallinity in a bulk of said metal alloy portion; and (iii) one or more metal atoms different from the first and second metal having a concentration profile evidencing diffusion into the metal alloy portion (see FIG. 6 described below).

As described above, MRI heating resistant surface structure can comprise in any order one or more of (i), (ii) and (iii), and a continuous or discontinuous lamellar nanostructure or microstructure structure, which can in one embodiment completely extend into the bulk of the metal alloy or device. For example, two or more of (i), (ii) and (iii) can also be combined, as well as with a continuous or discontinuous lamellar nanostructure or microstructure. For example, one or more atoms can be diffused into a matrix phase that already has a plurality of nanometer scale to micron scale particles, precipitates and/or inclusions.

The natural tendency of the atoms is to arrange themselves in a lattice. However, if the alloys are heated and then cooled very quickly in such a manner that the atoms do not have sufficient time to arrange themselves in a crystal lattice, then they may be considered partly or fully amorphous. As used herein, "a different level of crystallinity" refers to a change in average % crystallinity of at least 5%, wherein 100% represents a perfect crystal and 0% represents a fully amorphous state. As known in the art, a phase is a uniform portion of an alloy that has the same chemical and physical characteristics.

The distribution and size of precipitates, inclusions or particles refers to a second phase in the matrix of the first phase. A typical concentration range for the precipitates, inclusions or particles is to provide a volume fraction ≥3%. The second phase can range from nanometer scaled to micron scaled particles, precipitates or inclusions. These differ in chemical composition and physical characteristics from the matrix phase and may be a result of a chemical reaction between the alloy and the gases in contact with the surface or inherent products of the heat treatment from within the alloy.

Figure 3:
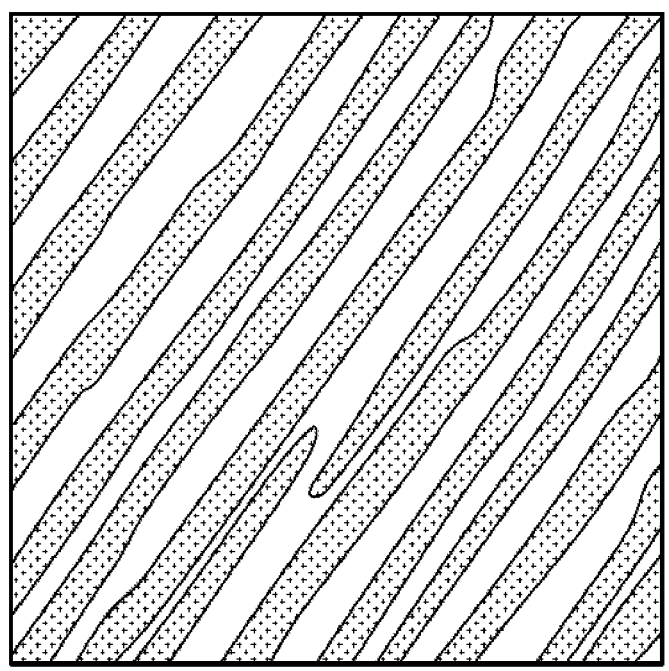
FIG. 3 shows a depiction of a metal alloy material having a nanostructure or microstructure that includes both continuous and discontinuous lamellar structures formed by a spinodal decomposition process, according to an embodiment of the invention.

The MRI heating resistant surface structure can include a continuous or discontinuous lamellar nanostructure or microstructure at the surface or throughout the bulk of the material (see FIG. 3). The metallic elements that constitute the alloys or have been introduced into the alloy are generally selected so as to form one or more phases when heated.

When subsequently cooled, one or more of the phase(s) can undergo decomposition into a continuous or discontinuous lamellar nanostructure or microstructure. The decomposition is generally a spinodal decomposition, eutectic or eutectoid reaction that can occur in a wide range of alloy systems. As known in the metallurgical arts, spinodal decomposition, eutectic or eutectoid reactions are methods by which a mixture of two or more materials can separate (i.e. segregate) into distinct regions with different material concentrations and form lamellar nanostructures or microstructures. The lamellar nanostructure or microstructure can be produced either on the surface of the alloy or device or throughout its bulk.

The elements comprising alloys according to disclosed embodiments are selected so as to produce non-magnetic alloys as defined above. In some cases, one or more ferromagnetic metals may be included in the alloy, provided the resulting alloy is non-magnetic. For example, as known in the art, Ni is ferromagnetic, but combines with Ti to form NiTi which is a non-magnetic alloy. Elemental additions may also be used that may be ferromagnetic provided in a concentration limited by the magnetically induced deflection force as a result of their addition remaining less than the force on the device or alloy due to gravity (its weight). These elements can be included to improve MR visibility and contrast and in some cases even allow for imaging of the tissues in regions between parts of the medical device or implant. For example elements such as Ag and Pd are known for this purpose in stents (See Lukas C. van Dijk, Jacqueline van Holten, Bastiaan P. van Dijk, Niels A. A. Matheijssen and Peter M. T. Pattynama, A Precious Metal Alloy for Construction of MR Imaging-compatible Balloon expandable Vascular Stents, Radiology 2001; 219:284-287).

Figure 1B:
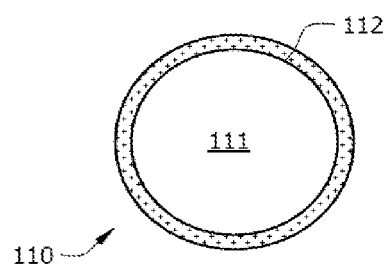
FIG. 1B is a cross sectional depiction of a wire in a lead shown in FIG. 1A showing a bulk that is compositionally and/or structurally different from the MRI heating resistant surface structure, according to a disclosed embodiment.

FIG. 1A is a depiction of a partially cut open exemplary medical device 100 that includes a battery 105, wherein a metal alloy portion provides leads 110 that include an MRI heating resistant surface structure that are coupled by connector pins 114 to the battery 105 for carrying current from the battery to one or more electrodes (not shown), according to a disclosed embodiment. Electronic circuitry 120 is also shown. FIG. 1B is a cross sectional depiction of one or more wires that form lead 110 shown in FIG. 1A evidencing a bulk portion 111 that is compositionally and/or structurally different from the MRI heating resistant surface structure 112, according to a disclosed embodiment. The leads are generally less than a few mm in diameter with wires in the leads generally being around tens to hundreds of microns in diameter.

Medical device 100 can comprise an implanted current carrying medical device such as a cardiac device (e.g., pacemaker) or a neuro-stimulator device. The MRI heating resistant surface structure 112 provides an increase of at least 10% in the magnitude of its impedance in the frequency range of the RF field (42.56 MHz per Tesla) as compared to the bulk 111 of the metal alloy portion.

Figure 2A:
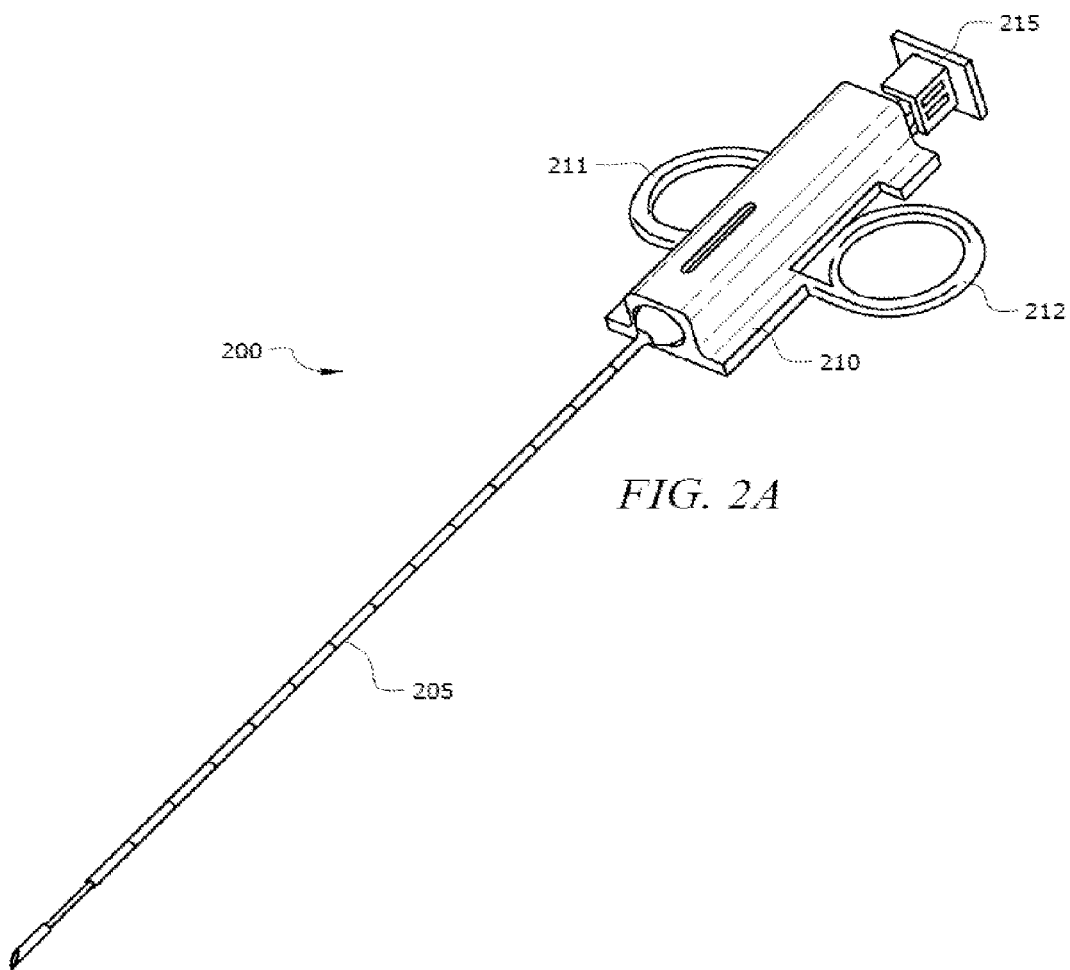

FIG. 2A is a depiction of an exemplary non-current carrying medical device shown as a biopsy needle device 200 for collecting a tissue specimen, wherein the needle 205 comprises a metal alloy portion that includes an MRI heating resistant surface structure, generally along its entire length. Biopsy needle device 200 also includes a handle body 210 that includes handles 211 and 212, and a plunger mechanism 215 that is operable to create a suction to draw a tissue specimen into the needle 205.

Figure 2B:
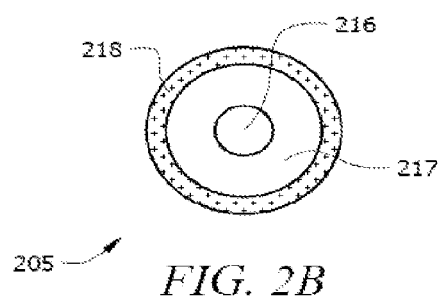
FIG. 2B shows bulk that is compositionally and/or structurally different from the MRI heating resistant surface structure, according to a disclosed embodiment.

FIG. 2B shows a cross sectional depiction of needle 205. Needle 205 includes hollow center region 216, a bulk portion 217 and a MRI heating resistant surface structure 218, according to a disclosed embodiment. In one embodiment, MRI heating resistant surface structure 218 includes a lamellar nanostructure or microstructure, and wherein the lamellar nanostructure or microstructure extends into both the MRI heating resistant surface structure 218 and the bulk portion 217. The MRI heating resistant surface structure 218 can include one or more metal atoms different from the first and second metal, such as Pt, Pd, Ag or Au, in a concentration of at least 0.1 atomic % (of the metal alloy) for increasing the MRI visibility of the needle 205. The one or more metal atoms different from the first and second metal, such as Pd or Ag, are generally not included in bulk portion 217.

The metal alloy can be processed and thermo mechanically treated generally using metallurgical techniques. Processing may also include forming (e.g., extruding) or casting the alloy material into a shape suitable for a device or implant, such as into wire or lead form.

Following forming into a suitable shape, a source of heat can then be applied to the surface of the metal alloy either in vacuum or in a controlled gaseous and/or temperature environment. The heating is generally performed at a temperature between that where diffusion processes are active in the time scale required for heating to where localized melting and/or chemical reaction at or below the surface occurs. Typical temperatures range from a third of the melting temperature of the alloy to the melting temperature of the alloy. Examples of such heat sources include a laser beam or wire typically used for electrical discharge machining. Other sources are furnaces with controlled gaseous environments. The heat can be applied either:

(i) continuously, or
(ii) intermittently (pulsed)

by either controlling the source of heat or the exposure of the alloy to the source of heat.

The processing can also first be accomplished in the metal alloy which is then subsequently formed into the shape of the medical device or implant.

The gaseous environment can be chosen to include elements that upon introduction into the base alloy or device provide one or more of the embodiments described above.

Processing parameters such as time, temperature, gaseous environment can be selected to create a microstructure in the alloy material that produces a MRI heating resistant surface structure comprising one or more of the following layers generally in any order from the surface of the metal alloy or device:

A layer such as that depicted in FIG. 3 according to an embodiment of the invention comprising a continuous or discontinuous lamellar nanostructure or microstructure as a result of a spinodal decomposition, eutectic or eutectoid reactions.

Figure 4:
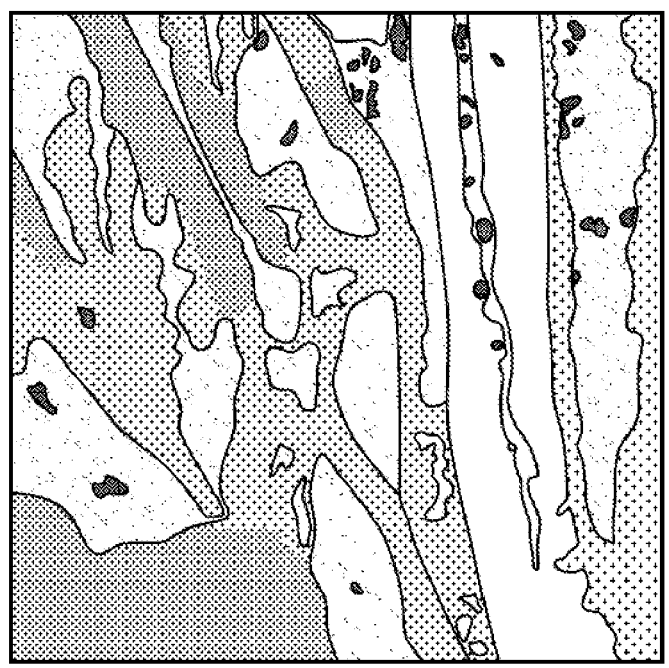
FIG. 4 shows a depiction of a metal alloy material that includes an outer surface layer having a high concentration of inclusions and a recast layer below the outer surface layer having a different level of crystallinity, according to another embodiment of the invention.

(ii) A layer such as that depicted in FIG. 4 according to an embodiment of the invention having a different level of crystallinity as compared to a level of crystallinity the bulk of the composition (as defined by the percentage of atoms that are arranged in a periodic and repeating three-dimensional array).

Figure 5:
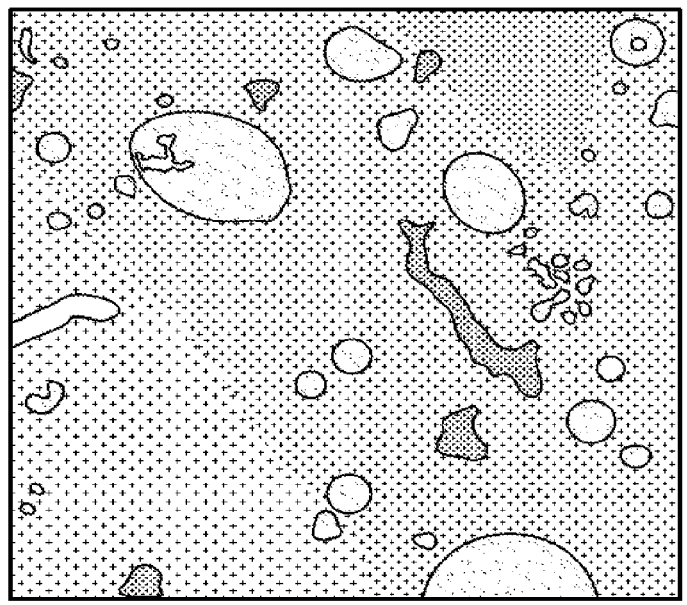
FIG. 5 is a depiction showing the microstructure of an exemplary outer surface layer according to another embodiment of the invention. The outer surface layer can be seen to include a plurality of precipitates, inclusions and particles.

(iii) A layer such as that depicted in FIG. 5 according to an embodiment of the invention comprising a matrix phase having a plurality of nanometer scale to micron scale particles, precipitates and/or inclusions therein, wherein the particles, precipitates or inclusions differ in chemical composition and physical characteristics from the matrix phase and are discontinuously distributed therein.

Figure 6:
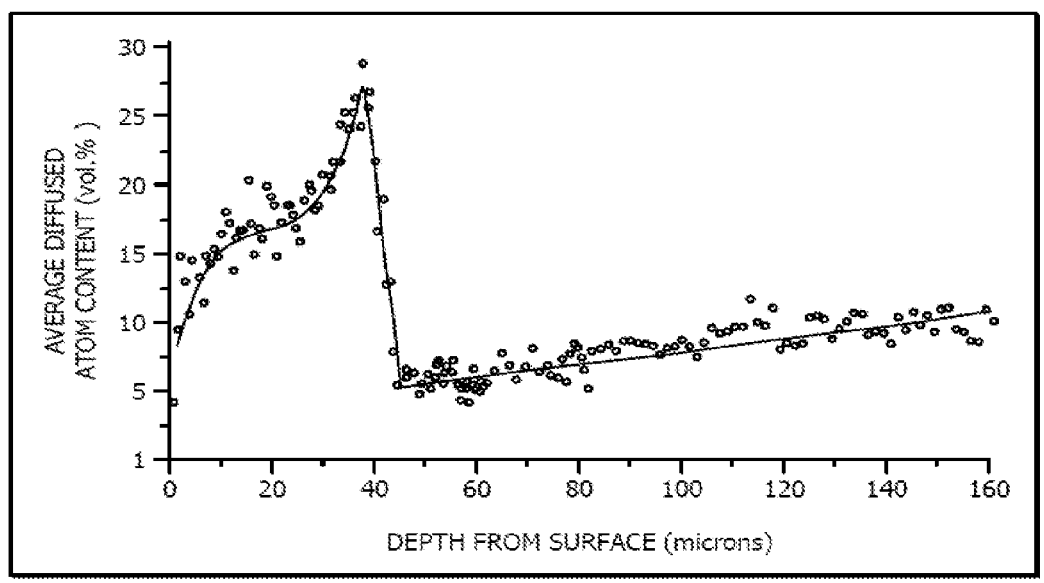
FIG. 6 is a depiction of a concentration profile of diffused atoms for a metal alloy material according to another embodiment of the invention.

(iv) A layer such as that depicted in FIG. 6 according to an embodiment of the invention containing one or more metal atoms different from the first and second metal atoms that have been diffused into the material.

One or more of the above (i)-(iv) can be provided generally in any order from the surface of the alloy or device. As described above, each of the layers can have a thickness of ≥3 nanometers typically up to several centimeters, and two or more layers can also be combined into one. For example, one or more metal atoms can be diffused into a matrix phase that already has a plurality of nanometer scale to micron scale particles, precipitates and/or inclusions.

FIG. 3 shows a depiction of the elemental addition and process control that causes a spinodal decomposition to result in a continuous and discontinuous lamellar nanostructure or microstructure. See K. T. Moore, W. C. Johnson, J. M. Howe, H. I. Aaronson and D. R. Veblen, On the interaction between Ag-depleted zones surrounding γ plates and spinodal decomposition in an Al-22 at. % Ag alloy, Acta Materialia 50 (2002) 943-956. The length scale of the features (layer thicknesses) can be from nanometers to centimeters.

FIG. 4 shows a depiction of a NiTi alloy material that includes an outer surface layer having a concentration of inclusions in a volume fraction ≥3% and a recast sub-surface layer below the surface layer having a different level of crystallinity as compared to the outer surface layer, according to another embodiment of the invention. The outer surface layer may contain precipitates, inclusions and/or particles in a volume fraction ≥3% as a result of the controlled gaseous and/or temperature environment the processing was carried out in. The length scale of the features can be from nanometers to centimeters.

FIG. 5 is a depiction showing the microstructure of an outer surface layer according to an embodiment of the invention. The outer surface layer (thickness range from nanometers to centimeters) can be seen to include a plurality of precipitates, inclusions and particles. The length scale of the features can be from nanometers to centimeters.

FIG. 6 is a depiction showing the concentration profile of diffusant Co atoms into the matrix. See Hardness profile measurements in functionally graded WC-Co composites by C. Larsson and M. Oden Materials Science and Engineering A 382 (2004) 141-149.

In some cases it may be desirable to remove a portion of the thicknesses of the outer surface layer and/or recast layer utilizing a removal process such as electropolishing. This purpose of surface removal is to tailor the surface of the alloy to tune the penetration depth of the RF field as well as the heating associated with currents induced by it so as to minimize heating while in an MRI environment.

By controlling the heating parameters and the gaseous and/or temperature environment (heating and cooling rate, hold time, concentration of one or more gases around the sample), one or more of the following for the MRI heating resistant surface structure can be controlled:

(i) the spacing and layer thickness of the continuous or discontinuous lamellar nanostructure or microstructure (e.g., see FIG. 3)

(ii) the level of crystallinity (e.g., see FIG. 4)

(ii) the distribution and size of precipitates, inclusions and particles (e.g., see FIG. 5);

(iii) the diffusion profile (e.g., FIG. 6)

so as to influence the penetration or skin depth of the incident RF field during MRI and the subsequent propagation of the induced currents. It is generally desirable to have as much of the incident RF energy associated with heating while in an MRI environment reflected away so that there are almost no resulting induced currents in the alloy or device. An alloy composition described herein can control the skin depth and the propagation of the resulting current so as to achieve this. As recognized by the Inventors, the skin or penetration depth and the MRI visibility can be influenced by the elements and/or structure present through that depth. The propagation of the resulting current and the associated heating is influenced by the impedance of the volume of the material through which the induced current propagates which is in turn influenced by the resulting structure resulting from the heating parameters and the gaseous and/or temperature environment (heating and cooling rate, hold time, concentration of one or more gases around the sample).

EXAMPLES

The following non-limiting prophetic example serves to illustrate selected embodiments of the invention. It will be appreciated that variations in proportions and alternatives in elements of the components shown will be apparent to those skilled in the art and are within the scope of embodiments of the present invention.

Consider a surgical needle. Standard metallurgical techniques known in the metallurgical arts, but unknown in the medical imaging and surgical arts, can be used to extrude and heat treat a bar of Al-22 wt. % Ag to produce a lamellar structure, such as depicted in FIG. 3. The lamellar structure in this example would extend through the bulk of the alloy. The alloy could then be extruded and electrical discharge machined (EDM) to fabricate a needle. EDM parameters (power and time) can be selected to control the surface microstructure similar to that depicted in FIG. 4 (which was for a NiTi alloy). The needle can then be tested using four ASTM standards to demonstrate MRI compatibility—F2052-06 for Measurement of Magnetically Induced Displacement Force on Medical Devices in the MR Environment, F2213-06 for Measurement of Magnetically Induced Torque on Medical Devices in the MR Environment, F2182-02a for Measurement of Measurement of Radio Frequency Induced Heating Near Passive Implants During MRI and ASTM F2119-01 for Evaluation of MR Image Artifacts from Passive Implants. Furnace heat treating in a gaseous environment can be carried out to diffuse atoms into the needle (such as in FIG. 6) to enhance MRI compatibility.

Consider the case of a current carrying conductor for implanting into the human body (e.g., a pacemaker lead). The wires that constitute the lead can be heated in one or more gaseous environments in a series of steps using a laser beam or in a controlled atmosphere furnace so as to obtain a profile of diffusant atoms such as shown in FIG. 6 to provide improved MRI compatibility, including a reduction of heating while in an MRI environment. In this application, the profile will generally be limited to a few microns in depth so as to not affect the current carrying capability of the inside of the wires. The wires can then be tested using four ASTM standards to demonstrate MRI compatibility—F2052-06 for Measurement of Magnetically Induced Displacement Force on Medical Devices in the MR Environment, F2213-06 for Measurement of Magnetically Induced Torque on Medical Devices in the MR Environment, F2182-02a for Measurement of Measurement of Radio Frequency Induced Heating Near Passive Implants During MRI and ASTM F2119-01 for Evaluation of MR Image Artifacts from Passive Implants. The wires can then be wound into leads for implantation in the human body.

While various disclosed embodiments have been described above, it should be understood that they have been presented by way of example only, and not limitation. Numerous changes to the disclosed embodiments can be made in accordance with the disclosure herein without departing from the spirit or scope of the invention. Thus, the breadth and scope of this disclosure should not be limited by any of the above described embodiments. Rather, the scope of this disclosure should be defined in accordance with the following claims and their equivalents.

Although embodiments of the invention has been illustrated and described with respect to one or more implementations, equivalent alterations and modifications will occur to others skilled in the art upon the reading and understanding of this specification and the annexed drawings. In addition, while a particular feature may have been disclosed with respect to only one of several implementations, such a feature may be combined with one or more other features of the other implementations as may be desired and advantageous for any given or particular application.

The invention claimed is:

1. An MRI compatible implantable medical device, comprising:
   at least one non-magnetic metal alloy portion, wherein said non-magnetic metal alloy portion comprises:
   a bulk portion including a first and at least a second metal different from said first metal;
   wherein a surface of said non-magnetic metal alloy portion includes an integral MRI heating resistant surface structure having a thickness >3 nanometers, and
   wherein said surface is structurally different from said bulk portion and comprises a lamellar nanostructure or microstructure.

2. The MRI compatible implantable medical device of claim 1, wherein said lamellar nanostructure or microstructure is continuous.

3. The MRI compatible implantable medical device of claim 1, wherein said lamellar nanostructure or microstructure is discontinuous.

4. The MRI compatible implantable medical device of claim 1, wherein said lamellar nanostructure or microstructure extends into both said MRI heating resistant surface structure and said bulk portion.

5. The MRI compatible implantable medical device of claim 1, wherein said MRI heating resistant surface structure is compositionally different from said bulk portion and further comprises at least one of:
   (i) a matrix phase comprising said first and said second metal having a plurality of nanometer scale to micron scale particles, precipitates and/or inclusions therein constituting a volume fraction >3%, wherein said particles, precipitates or inclusions differ in chemical composition and physical characteristics from said matrix phase and are discontinuously distributed therein;
   (ii) a level of crystallinity that is at least 5% less as compared to a level of crystallinity in said bulk portion of said non-magnetic metal alloy portion; and
   (iii) one or more metal atoms different from said first and second metal having a concentration profile evidencing diffusion which varies as a function of distance into said non-magnetic metal alloy portion.

6. The MRI compatible implantable medical device of claim 5, wherein said MRI heating resistant surface structure comprises said (iii) one or more metal atoms different from said first and second metal having a concentration profile evidencing diffusion which varies as a function of distance into said non-magnetic metal alloy portion.

7. The MRI compatible implantable medical device of claim 6, wherein one or more different metal atoms from said first and second metal is in a concentration of at least 0.1 atomic % for increasing MRI visibility of said non-magnetic metal alloy portion.

8. The MRI compatible implantable medical device of claim 7, wherein said metal atoms different from said first and second metal comprise Au, Pt, Pd or Ag.

9. The MRI compatible implantable medical device of claim 1, further comprising a battery, wherein said non-magnetic metal alloy portion is in leads that are coupled to said battery for carrying current from said battery.

10. The MRI compatible implantable medical device of claim 9, wherein said leads comprise cardiac leads for a cardiac device or neuro-stimulator leads for a neuro-stimulator device.

11. The MRI compatible implantable medical device of claim 5, wherein said MRI heating resistant surface structure includes said (i) matrix phase comprising said first and said second metal having a plurality of nanometer scale to micron scale particles, precipitates and/or inclusions therein constituting a volume fraction >3%, wherein said particles, precipitates or inclusions differ in chemical composition and physical characteristics from said matrix phase and are discontinuously distributed therein.

12. The MRI compatible implantable medical device of claim 5, wherein said MRI heating resistant surface structure includes said (ii) level of crystallinity that is at least 5% less as compared to a level of crystallinity in said bulk portion of said non-magnetic metal alloy portion.

13. The MRI compatible implantable medical device of claim 1, wherein said integral MRI heating resistant surface structure provides an increase of at least 10% in a magnitude of its impedance in a frequency range of an RF field of 42.56

MHz per Tesla as compared to said bulk portion for reduced heating of said surface from current induced by said RF field.

* * * * *